United States Patent [19]

Braun

[11] Patent Number: 4,462,399

[45] Date of Patent: Jul. 31, 1984

[54] POWERED AIR RESPIRATOR AND CARTRIDGE

[75] Inventor: David L. Braun, Lake Elmo, Minn.

[73] Assignee: Minnesota Mining and Manufacturing Company, St. Paul, Minn.

[21] Appl. No.: 307,872

[22] Filed: Oct. 2, 1981

[51] Int. Cl.$^3$ ........................ A61F 9/06; A61M 15/00

[52] U.S. Cl. .......................... 128/201.25; 128/201.24; 55/497; 55/DIG. 35

[58] Field of Search ....................... 128/205.12, 205.29, 128/201.12, 201.23, 201.24, 201.25, 201.29, 206.19, 206.16; 2/171.3, 424; 55/103, 131, 132, 385 R, 385 F, 497, DIG. 35, 499; 604/405, 406

[56] References Cited

U.S. PATENT DOCUMENTS

| | | | |
|---|---|---|---|
| 2,800,195 | 7/1957 | Bub | 55/499 |
| 3,138,433 | 6/1964 | Engle et al. | 55/499 |
| 3,372,533 | 3/1968 | Rummel | 55/499 |
| 3,613,678 | 10/1971 | Mayhew | 128/206.19 |
| 3,803,810 | 4/1974 | Rosenberg | 604/406 |
| 3,853,529 | 12/1974 | Boothe et al. | 55/499 |
| 3,971,373 | 7/1976 | Braun | 128/206.19 |
| 4,021,353 | 5/1977 | Raines et al. | 604/406 |
| 4,149,549 | 4/1979 | Grossman | 55/103 |
| 4,215,682 | 8/1980 | Kubik et al. | 128/206.19 |
| 4,278,084 | 7/1981 | Pope, Jr. | 604/406 |
| 4,280,491 | 7/1981 | Berg et al. | 128/201.25 |
| 4,294,599 | 10/1981 | Grovesteen et al. | 55/DIG. 35 |

FOREIGN PATENT DOCUMENTS

| | | | |
|---|---|---|---|
| 2431197 | 2/1975 | Fed. Rep. of Germany | 55/103 |

*Primary Examiner*—Richard J. Apley
*Assistant Examiner*—Harry J. Macey
*Attorney, Agent, or Firm*—Donald M. Sell; James A. Smith; Lorraine R. Sherman

[57] ABSTRACT

A high efficiency rigid or semi-rigid air filter cartridge for use in the helmet of a powered air respirator comprising a lightweight, open-topped, trough-shaped frame having an entrance at one end for attachment to an air discharge port of a fan motor housing assembly, filter media sealed about its periphery to close said frame, said frame and said filter media enclosing a contaminated air plenum bounded by the inside surfaces of the bottom and side walls of said frame and the under surface of said filter media, such that contaminated air from said air discharge port is channeled under pressure through said plenum and distributed under pressure to and through said filter media and provides purified air, is disclosed. The filter media may be a sorbent particle loaded web, an electrically charged filter, or pleated fiberglass paper. A high efficiency powered air respirator for providing filtered air to a wearer, is also disclosed. The powered air respirator includes the rigid or semi-rigid air filter cartridge of the invention as well as improved sealing means between the respirator parts.

16 Claims, 5 Drawing Figures

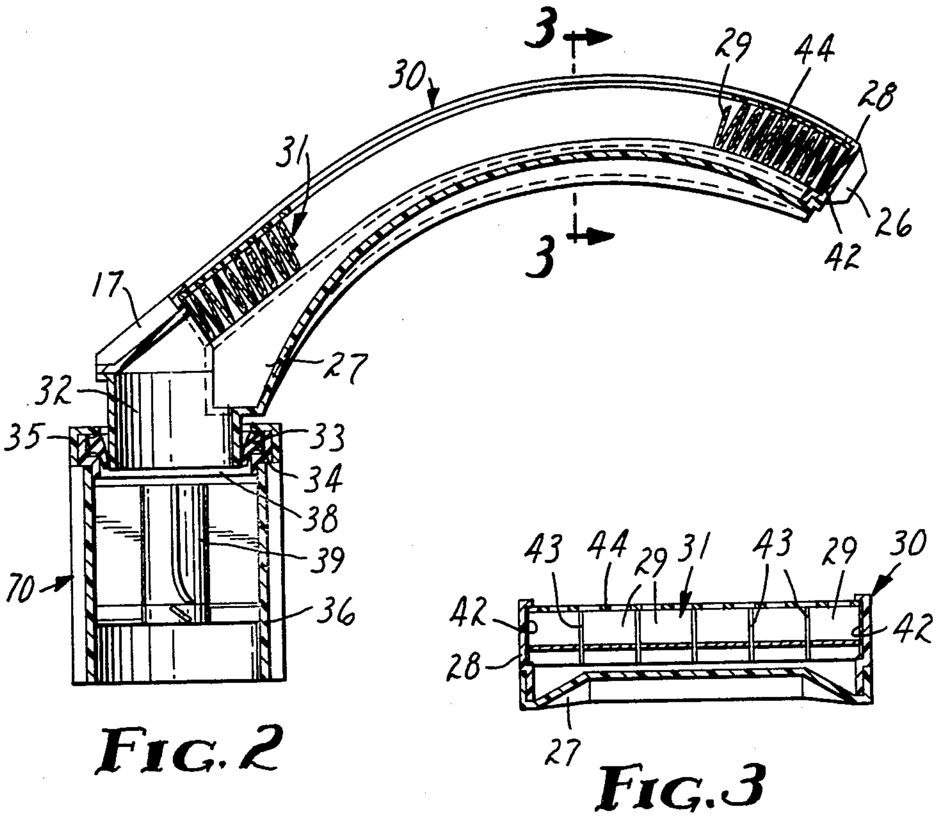
FIG. 2
FIG. 3
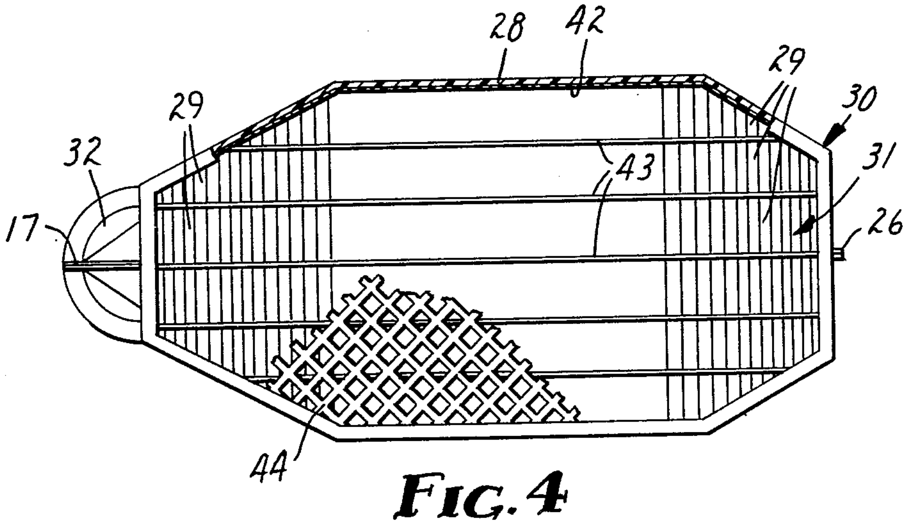
FIG. 4

POWERED AIR RESPIRATOR AND CARTRIDGE

DESCRIPTION

1. Technical Field

The present invention relates to filter cartridges and to improvements in powered air respirators utilizing such cartridges for use in atmospheres contaminated by toxic dusts, mists, gases, vapors, airborne radioactive substances, or fumes.

2. Background Art

There is increasing interest by government agencies, the general public, and the workforce in protecting individuals against the harmful effects of toxic materials. Back and belt mounted high performance powered air respirators are known in the art but they suffer from certain shortcomings. Back and belt mounted air respirators connected to separate breathing devices are heavier, cause the wearer to suffer greater loss of mobility in confined areas, and are more costly than a completely self-contained, in-helmet powered air respirator. The Racial Airstream, Type AH3, high efficiency air respirator system (Racial Airstream Inc., Rockville, MD) utilizes such a back or belt mounted unit. A second high efficiency powered air respirator is the Martindale Mark IV (Martindale Protection Ltd., London) which is equipped with Type HEF filters and it also is back mounted. The *Occupational Safety and Health Reporter* in its Aug. 6, 1981 issue pointed out that back and belt mounted units frequently fail to protect the worker properly due to equipment failure when filters are jarred loose as the wearer brushes against a wall or piece of equipment. This type of problem is eliminated by the "filter in helmet" concept.

Helmets with internal air filtration systems known in the art are limited to devices utilizing conformable filter materials, most often of the bag type. U.S. Pat. No. 4,280.491, utilizes a bag type filter in a powered air respirator. Other patents disclosing comformable filter materials in air filtering helmets are U.S. Pat. Nos. 3,963,021 and 3,822,698 and U.K. Pat. No. 1,426,432. The Racial Airstream AH.1 (Racal Airstream Inc., Rockville, MD), an anti-dust powered air respirator, likewise has an in-helmet comformable bag-type filter. None of these respirators provide high efficiency filtration.

Attempts to use conformable filters in higher grade filtering applications for utility in atmospheres contaminated by metal fume and airborne radioactive substances have not been successful. As more conformable media is added in order to increase the filtration efficiency and meet the more stringent performance levels required, the media begin to conform and pack into the limited available space, thereby restricting airflow. Increasing the space used for the conformable filter media subtracts from the space available for airflow. In sum, the property of conforming to the limited available space permits the success of conformable filters in lower grade applications but bars their success for higher grade applications. Also, the uncertainty of position taken by the conformable media increases the probability that blocking of air flow pathways will occur.

High performance filter media such as adsorbent particle loaded webs (disclosed in U.S. Pat. No. 3,971,373) and pleated fiberglass paper media (disclosed in French Pat. No. 1,099,000) are known in the art. However, these filter media have not been successfully used, prior to the present invention, within the helmet in a powered air respirator.

There is a need for high performance in-helmet type powered air respirators that are capable of meeting stringent government standards for respiratory protection. Particularly, there is need for protection against highly toxic particulate materials such as arsenic, radio nuclides, platinum, beryllium, and high levels of lead and asbestos. The summation of leakage from all components in the air filtering pathway must not exceed 0.03 percent, i.e., 99.97 percent filtering efficiency is required, based on testing against 0.3 micron dioctylphthalate (DOP) particles. For protection against toxic gases and vapors such as toluene, methylethylketone, trichloroethylene, 1,1,2-trichloroethane, and isophorone, the maximum leakage must be less than 5 parts per millon (ppm) by volume based on testing at 1000 ppm carbon tetrachloride over a 50 minute period. Until now, no powered air supplying helmet with in situ filtration has met the above requirements.

DISCLOSURE OF THE INVENTION

The present invention represents improvements over the powered air respirator disclosed in U.S. Pat. No. 4,280,491, which patent is incorporated herein by reference.

The present invention provides a high efficiency rigid or semi-rigid air filter cartridge for use in the helmet of a powered air respirator comprising a lightweight, open-topped, trough-shaped frame having an entrance at one end for attachment to an air discharge port of a fan motor housing assembly, filter media sealed about its periphery to close said frame, said frame and said filter media enclosing a contaminated air plenum bounded by the inner surfaces of the bottom and side walls of said frame and the under surface of said filter media, such that contaminated air from said air discharge port is channeled under pressure through said plenum and distributed under pressure to and through said filter media and provides purified air. The filter media may be a sorbent particle loaded web, an electrically charged filter, or a pleated fiberglass paper which may be retained in pleated form by glue string spacers, as is described in detail below.

The present invention also provides a high efficiency powered air respirator for providing filtered air to a wearer, said respirator comprising a hardhat with an overlying shell member secured to said hardhat and spaced therefrom to form a dome-shaped cavity between said hardhat and said shell member, a face shield assembly hingeably attached to and depending from the front of said shell member, air circulating means including a fan motor housing with an air discharge port at one end thereof, said air circulating means located in the rear portion of said dome-shaped cavity, a rigid or semi-rigid, disposable air filter cartridge, as described above, located in said dome-shaped cavity and comprising a lightweight frame with filter media sealed about its periphery to close said frame, said frame and said filter media enclosing a contaminated air plenum bounded by the inner surfaces of the bottom and side walls of said frame and the under surface of said filter media, said filter cartridge being sealably connected at one end to an air discharge port of a fan motor housing assembly by a seal capable of completely isolating said contaminated air plenum from said dome-shaped cavity, and a clean air passageway comprising the remaining space in said dome-shaped cavity, said air discharge port of said fan motor housing providing contaminated air under pressure from said air circulating means into and through said contaminated air plenum and into and through said filter media to deliver purified air to said clean air passageway, said clean air passageway having openings at one end for delivering purified air to said face shield assembly thereby providing clean air in a stream over the wearer's face.

In one embodiment, the filter cartridge contains pleated fiberglass paper filter media (20 mm Filtrapleate, Tri-Dim Filter Corp., Hawthorne, N.J.). The fiberglass filter paper media used is 1 mm thick and there are about three pleats per cm, the height of each pleat being 20 mm, although pleated fiberglass paper and pleating of other dimensions are envisioned within the present invention. The pleats are retained in position by glue string spacers. Such a filter cartridge is capable of providing at least 99.97 percent filtering efficiency for 0.3 micron dioctylphthalate (DOP) particles.

In another embodiment, the filter cartridge contains a sorbent particle loaded web as taught in U.S. Pat. No. 3,971,373, which patent is hereby incorporated herein by reference. The sorbent particle loaded web is a porous sheet product containing a supported threedimensional arrangement of particles, which particles may be any adsorbent such as activated carbon, alumina, or silica gel, or they may be a catalytic material such as hopcalite. This sheet product, in which essentially the full surface area of the particles is available for interaction with a medium to which the sheet product is exposed, comprises a web of melt-blown microfibers (very fine fibers prepared by extruding molten fiber-forming material through fine orifices in a die into a highvelocity gaseous stream) and the particles themselves. No additional binder material to adhere the particles to the fibers is necessary. Such a filter cartridge provides at least 99.5 percent filtering efficiency for $CCl_4$ vapor (i.e., it is required that not more than 5 ppm of $CCl_4$ for a 50 minute period pass through the filter media when tested at a minimum of 170 lpm of 1000 ppm $CCl_4$ in air).

The filter cartridge may be bowed, curved, or flat or of any other desired shape that enables it to fit within the dome-shaped cavity provided in the powered air respirator of the present invention. The frame of the filter cartridge is lightweight, preferably of plastic or metal, and desirably is U-shaped in cross-section although other shapes fitting within the dome-shaped cavity are envisioned and are within the present invention.

In order to achieve high efficiency particulate air (H.E.P.A.) level performance towards particulate matter or high efficiency towards gas and vapor filtration, the high efficiency powered air respirator of the present invention provides a novel high performance filter cartridge as well as improved quality of sealing between the respirator parts, i.e., a seal connecting the fan motor housing assembly to the filter cartridge, which seal may have multiple parts and is made of no. 70 durometer neoprene rubber or other material of similar durometer capable of resisting a wide range of toxic vapors at low concentrations. Improved electrical connections in the fan motor housing are also provided.

BRIEF DESCRIPTION OF THE DRAWINGS

FIG. 2 is a longitudinal sectional view of one embodiment of the motor and air filter mechanism of the powered air respirator of FIG. 1;

FIG. 3 is a sectional view along the line 3—3 of FIG. 2; and

FIG. 4 is a top plan view, with parts thereof broken away, of the filter cartridge of the powered air respirator of FIG. 1.

DETAILED DESCRIPTION OF THE INVENTION

Figure 1:
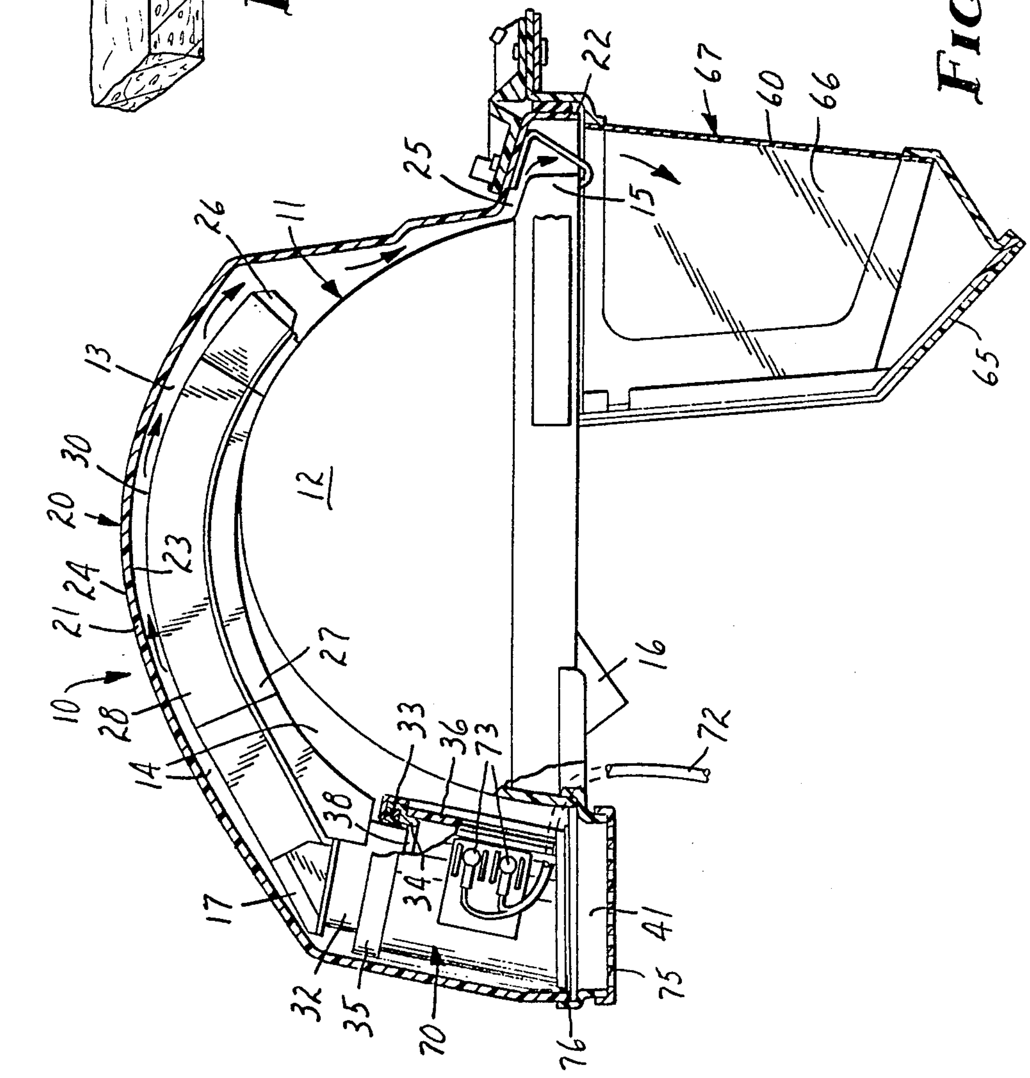
FIG. 1 is a vertical sectional view of the powered air respirator with some parts shown in elevation.

Referring to the drawings and particularly FIGS. 1 and 2, the powered air respirator 10 of the present invention comprises a safety helmet or hardhat 11, an outer shell member 20 having overall dimensions greater than hardhat 11 spaced from and overlying the hardhat thus forming a generally dome-shaped cavity 13 between the outer shell member 20 and hardhat 11, air filter cartridge 30 located in the dome-shaped cavity, a protective face shield assembly 67 attached to and depending from the front of outer shell member 20, a transparent face shield 60 mounted in the face shield assembly 67, face sealing means 65 to seal against a user's face from the temple, down across the bottom of the chin and up to the temple, and air circulating means 70 located in the rear portion of dome-shaped cavity 13.

Hardhat 11 comprises a rigid shell 12 of high density polyethylene of generally dome-shaped configuration and is formed with a visor 15 at its front end. A head supporting harness 16 is removably fastened to inner part of rigid shell 12. Head supporting harness 16 is made adjustable at the back to fit various head sizes.

Hardhat 11 is an approved safety helmet and may be worn alone where hardhat protection is mandated or desired. When respiratory protection is required, hardhat 11 is mated to the remainder of the components and thus is used as a powered air respirator 10 with hardhat protection.

Outer shell member 20 comprises a generally dome-shaped rigid shell 21 vacuum-formed from a high impact polystyrene sheet 3.3 mm (0.13 inch) thick having an inner surface 23 and an outer surface 24 with a visor 22 at its front end and is dimensioned to be larger than rigid shell 12 of hardhat 11, as clearly shown in the drawings.

As shown in FIG. 1, the inner surface 23 of outer shell member 20 is spaced from the outer surface of hardhat 11 when the two members are in superposed position thus forming generally dome-shaped cavity 13. Dome-shaped cavity 13 contains therein filter cartridge 30, air circulating means 70, and irregularly shaped clean air passageway 14, said passageway comprising the remaining space in said dome-shaped cavity 13.

In the embodiment of the invention illustrated in FIGS. 1 and 2, air filter cartridge 30 which includes lightweight, trough-spaced frame 28, filter media 31, and contaminated air plenum 27 formed by the inner surfaces of the bottom and side walls of said frame and the under surface of said filter media, is positioned in dome-shaped cavity 13. Purified air is delivered under pressure from air filter cartridge 30 to clean air passageway 14 and enters slotted openings 25 and then face shield assembly 67. Slotted opening 25 is provided across the entire frontal area between the visor portion 15 of hardhat 11 and the visor portion 22 of inner surface 23 of outer shell member 20. Air filter cartridge 30 with filter media 31 therein is typically disposable, the filter media made of pleated fiberglass 29, e.g., 20 mm Filtrapleate (1 mm thick fiberglass paper), available from Tri-Dim Filter Corp., Hawthorne, N.J., there being 3 pleats/cm and the height of each pleat being 20 mm, pleated fiberglass 29 being retained in pleated form by spacers 43, as is shown in FIGS. 3 and 4. The use of other media such as sorbent loaded webs are all envisioned. These filtering means have superior filtering efficiency and low pressure drop characteristics. Expanded grill 44, preferably of light weight metal, protects pleated fiberglass 29 against externally caused damage that could cause leakage of contaminated air through the filter. As shown in FIG. 1 and 4, at the front edge of filter cartridge 30 is front tab 26 and at the rear edge is rear tab 17, said tabs being provided to enable securing of left and right halves of air filter cartridge 30 together with pleated fiberglass 29 between. As is shown in FIG. 3, glue channels 42 are provided to totally seal the periphery of filter media 31 to the side, front, and rear edges of trough-shaped frame 28 to prevent leakage of contaminated air into clean air passageway 14.

Contaminated air enters filter cartridge 30 through contaminated air plenum entrance 32. Fan motor housing assembly to filter cartridge seal 33 blocks contaminated air from entering clean air passageway 14 and allows for facile replacement of air filter cartridge 30. Seal 33 slidably connects air filter cartridge 30 with fan motor housing assembly 36 at air discharge port 38. Seal 33 surrounds the lower edge of contaminated air plenum entrance 32 and is itself surrounded by inner seal retainer 34 and outer seal retainer 35, which are glued together, and house seal 33, thereby forming a tight connection between air filter cartridge 30 and fan motor housing assembly 36. Seal 33, is made of no. 70 durometer neoprene rubber, and seal retainers 34 and 35 are made of high impact polystyrene. Air circulating means 70 moves contaminated air through fan motor housing entrance 41, through fan motor housing assembly 36, through air discharge port 38 and into and through contaminated air plenum entrance 32, into contaminated air plenum 27, and into filter media 31. Filter media 31 removes fumes, dust, mist, and particulates and allows filtered clean air to enter clean air passageway 14, pass through slotted opening 25 and enter face shield assembly 67 so as to stream across the face of the wearer. Air in passageway 14 is free of contaminants and is pressurized, thereby forcing air forward and through slotted opening 25. Face sealing means 65 prevents contaminated air from entering the face shield assembly 67 and breathing zone 66, and provides air exit areas as described in U.S. Pat. No. 4,280,491, column 3, line 64, to column 4, line 29.

Figure 5:
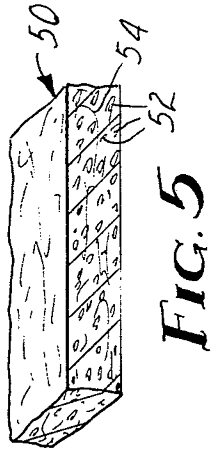
FIG. 5 is a perspective view of a second embodiment of the powered air respirator of FIG. 1.

In a second embodiment, FIG. 5 shows a microfibrous web 50, in blanket form, having sorbent particles 52 trapped within microfibers 54, which web can be positioned in filter cartridge 30 and adhesively secured to glue channels 42.

Air circulating means 70 comprises fan motor housing assembly 36, fan motor housing entrance 41, fan motor 39, and air discharge port 38 and is powered as is described in U.S. Pat. No. 4,280,491, column 4, lines 30–48. Electrical energy for fan motor 39 is delivered through internal electrical tab and socket connectors (not shown) which sealably connect to external tab and socket connectors 73 on the external surface of air circulating means 70. Power cord 72 joins external connectors 73 to batteries worn by the wearer (e.g., on a belt or pocket), External connectors 73 which are sealably joined to internal connectors (not shown) prevent contaminated air from entering clean air passageway 14. Mating pairs of all tab and socket connectors used are of different sizes so as to facilitate polarizing the electrical system. Fan motor housing base seal 76 prevents leakage of contaminated air from the fan motor housing assembly 36 into clean air passageway 14. Foraminous cover member 75 fits over fan motor housing entrance 41 to protect fan motor 39 from large objects entering it.

Protective face shield assembly 67 is described in detail in U.S. Pat. No. 4,280,491, column 3, lines 35–63.

The high level of efficiency mandated under U.S. government regulations as specified in Code of Federal Regulations (30 C.F.R. 11.140-11) for proper protection of individuals working in highly hazardous environments (depending on the degree of toxicity, it is necessary to remove up to 99.97% of the toxic particulate material by weight and up to 99.5% of toxic vapors) requires that the powered air respirator provide air free of contamination into the breathing zone. The procedures followed in testing the powered air respirator of the present invention for various types of failure which can result in entry of contaminated air into the breathing zone are described in the following examples.

Example 1—H.E.P.A. Filter Cartridge

The potential leakage pathways for the H.E.P.A. filter cartridge 30 of the present invention are (1) filter media leakage and (2) filter edge seal leakage. Both were tested by constructing filter cartridges as shown in FIGS. 2, 3, and 4 using vacuum formable polystyrene as the frame 28 for the filter cartridge. Frame 28 was bonded to 20 mm Filtrapleate fiberglass paper material using Silastic L silicon rubber (Dow Corning) as the sealant. The completed cartridge was connected to a 0.3 micron diameter dioctylphthalate (DOP) aerosol supply using wax to ensure a leak-free seal. At a flow rate of 85 lpm and a DOP concentration of 100 mg/m$^3$, the percent DOP penetration was read after 30 seconds using a Q127 DOP Penetrometer (Air Techniques Inc., Baltimore, MD).

TABLE I

HEPA Filter Cartridge Test Results
Using 0.3 Micron Diameter DOP Aerosol
At a Concentration of 100 mg/m$^3$ at 85 lpm

| Cartridge No. | Penetration (Percent) | Efficiency (Percent) |
|---|---|---|
| 1 | 0.004 | 99.996 |
| 2 | 0.020 | 99.980 |
| 3 | 0.003 | 99.997 |
| 4 | 0.005 | 99.995 |
| 5 | 0.007 | 99.993 |

The data in Table I show that H.E.P.A. filter cartridges of the present invention met the 99.97 percent H.E.P.A. efficiency requirement.

Example 2—Gas/Vapor Filter Cartridge

A cartridge filter for gas and vapor applications was made as described in Example 1 except that an activated carbon, blown micro-fiber loaded web, made by the teachings of U.S. Pat. No. 3,971,373, was used instead of the Filtrapleate media. The loaded web was 25 mm thick and contained 5800 grams per m$^2$ of Type 975 activated charcoal 30×80 mesh (Witco Chemical Corp.). The completed cartridge was connected to a 175 lpm supply of 1000 ppm $CCl_4$ in air at 50 percent R.H. The concentration of $CCl_4$ exiting the filter cartridge was read using a Type 30-100 Total Hydrocarbon Analyzer (Process Analyzers, Inc., Princeton, NJ).

TABLE II

Gas and Vapor Cartridge Test Results Using $CCl_4$ Vapor at a Concentration of 1000 PPM and at 175 lpm

| Time (min) | Breakthrough Concentration (PPM) | Efficiency (Percent) |
|---|---|---|
| 0 | 0 | 100.0 |
| 10 | 0 | 100.0 |
| 20 | 0 | 100.0 |
| 30 | 0 | 100.0 |
| 40 | 0 | 100.0 |
| 50 | 0 | 100.0 |
| 55 | 2 | 99.80 |
| 59.2 | 5 | 99.50 |

The data in Table II show that the total breakthrough was under 5 ppm for the required 50 minute duration.

Example 3—Fan Motor Housing Leakage

The fan motor housing assembly has three potential leakage pathways. These are 1) fan motor housing to filter seal, 2) the electrical feedthroughs, and 3) the fan motor housing base seal. All three potential leaks were tested using the challenge and cartridge as described in Example 1. Test data indicated that there was no change in DOP penetration for cartridges tested indicating that these three potential leakage pathways each exhibited no detectable leakage.

Example 4—Dust Loading

A silica dust loading test was conducted to show the ability of the cartridge filters to operate in dusty environments. Two filter cartridges, made as described in Example 1, were fitted, in separate trials, to the powered air respirator 10, as shown in FIG. 1, mounted on a mannequin. A freshly charged battery pack having four rechargeable nickel cadmium D-cells with a total output of 4.0 ampere hours at a nominal voltage of 4.8 volts was used. At an average room concentration of 53 to 54 mg/m$^3$ of silica dust, both filter cartridges met the flow requirements of 6.0 SCFM or better over a 4 hour period. For one cartridge the initial and final flow rates were 9.8 and 7.6 SCFM, respectively, and for the other cartridge the corresponding flow rates were 9.3 and 7.4 SCFM.

I claim:

1. A high efficiency rigid or semi-rigid air filter cartridge for use in the helmet of a powered air respirator, said air filter cartridge comprising:

a lightweight, hollow frame having a closed bottom which is curved, side walls, an open top, and having filter media mounted across the top of said frame constituting the upper surface of said cartridge, said frame and said filter media forming a contaminated air plenum having one entrance to receive contaminated air into one end of said air filter cartridge from an air discharge port of a fan motor housing assembly, said filter media being sealed about the periphery of said open topped frame to close said frame, and said contaminated air plenum being bounded by the inner surfaces of the bottom and side walls of said frame and the inside surface of said filter media, contaminated air from said air discharge port being channeled under pressure through said entrance to said frame and said contaminated air plenum of said filter cartridge and distributed under pressure to and through said contaminated air plenum and said filter media to provide purified air.

2. The filter cartridge according to claim 1 wherein said filter media is pleated fiberglass paper.

3. The filter cartridge according to claim 2 wherein said filter media is capable of trapping at least 99.97 percent of 0.3 micron diameter dioctylphthalate particles.

4. The filter cartridge according to claim 2 wherein said pleated fiberglass paper filter media is 1 mm thick, has three pleats per cm, the height of each pleat being 20 mm, and is capable of trapping at least 99.97 percent of 0.3 micron diameter dioctylphthalate particles.

5. The filter cartridge according to claim 1 wherein said filter media is a sorbent particle loaded web.

6. The filter cartridge according to claim 5 wherein said filter media is capable of providing at least 99.5 percent filtering efficiency toward $CCl_4$ vapors.

7. The filter cartridge according to claim 5 wherein said sorbent particle loaded web filter media is a blown micro-fiber loaded web which is 25 mm thick, contains 5800 g/m$^2$ of 30×80 mesh activated charcoal, and is capable of providing at least 99.5 percent filtering efficiency toward $CCl_4$ vapors.

8. A high efficiency powered air respirator for providing filter air to a wearer, said respirator comprising:

(a) a hardhat and an overlying shell member secured to said hardhat and spaced therefrom to form a dome-shaped cavity between said hardhat and said shell member, (b) a face shield assembly hingeably attached to and depending from the front of said shell member, (c) air circulating means including a fan motor housing with an air discharge port at one end thereof, said air circulating means located in the rear portion of said dome-shaped cavity, (d) a rigid or semi-rigid, disposable, high efficiency, air filter cartridge located in said dome-shaped cavity, said air filter cartridge comprising:

a lightweight, hollow frame having a closed bottom which is curved, side walls, an open top, and having filter media mounted across the top of said frame, said frame and said filter media forming a contaminated air plenum having one entrance to receive contaminated air into one end of said air filter cartridge from an air discharge port of a fan motor housing assembly, said filter media being sealed about the periphery of said open topped frame to close said frame, and said contaminated air plenum being bounded by the inner surfaces of the bottom and side walls of said frame and the inside surface of said filter media, contaminated air from said air discharge port being channeled under pressure through said entrance to said frame and said contaminated air plenum of said filter cartridge and distributed under pressure to and through said contaminated air plenum and said filter media to provide purified air, and (e) a clean air passageway comprising the remaining space in said dome-shaped cavity, said air discharge port of said fan motor housing providing contaminated air under pressure from said air circulating means into said contaminated air plenum entrance and through said contaminated air plenum and into and through said filter media to deliver purified air to said clean air passageway, said clean air passageway having openings at one end for delivering purified air to said face shield assembly thereby providing clean air in a stream over the wearer's face.

9. The respirator according to claim 8 wherein said filter media is pleated fiberglass paper.

10. The respirator according to claim 9 capable of trapping at least 99.97 percent of 0.3 micron diameter dioctylphthalate particles.

11. The respirator according to claim 10 wherein said pleated fiberglass paper filter media is 1 mm thick, has three pleats per cm, and the height of each pleat is 20 mm.

12. The respirator according to claim 9 wherein said pleated fiberglass paper filter media is 1 mm thick, has three pleats per cm, the height of each pleat being 20 mm, and is capable of trapping at least 99.97 percent of 0.3 micron diameter dioctylphthalate particles.

13. The respirator according to claim 8 wherein said filter media is a sorbent particle loaded web.

14. The respirator according to claim 13 capable of providing at least 99.5 percent filtering efficiency toward $CCl_4$ vapors.

15. The respirator according to claim 13 wherein said sorbent particle loaded web filter media is a blown micro-fiber loaded web which is 2.5 mm thick, contains 5800 g/m$^2$ of 30×80 mesh activated charcoal, and is capable of providing at least 99.5 percent filtering efficiency toward $CCl_4$ vapors.

16. The respirator according to claim 14 wherein said sorbent particle loaded web filter media is a blown micro-fiber loaded web which is 2.5 mm thick, and contains 5800 g/m$^2$ of 30×80 mesh activated charcoal.

* * * * *

UNITED STATES PATENT AND TRADEMARK OFFICE

CERTIFICATE OF CORRECTION

PATENT NO. : 4,462,399

DATED : July 31, 1984

INVENTOR(S) : David L. Braun

It is certified that error appears in the above-identified patent and that said Letters Patent is hereby corrected as shown below:

In Column 1, line 22 "Racial" should be --Racal--

In Column 1, line 23 "Racial" should be --Racal--

In Column 1, line 43 "Racial" should be --Racal--

Signed and Sealed this

*Ninth* Day of *July 1985*

[SEAL]

*Attest:*

DONALD J. QUIGG

*Attesting Officer* *Acting Commissioner of Patents and Trademarks*